United States Patent
Pazenok et al.

(10) Patent No.: US 10,125,103 B2
(45) Date of Patent: Nov. 13, 2018

(54) METHOD FOR PREPARING 5-FLUORO-1H-PYRAZOLE-4-CARBONYL FLUORIDES

(71) Applicant: Bayer CropScience Aktiengesellschaft, Monheim am Rhein (DE)

(72) Inventors: Sergii Pazenok, Solingen (DE); Hans Martin Thomas, Leichlingen (DE); Frank Volz, Köln (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/569,681

(22) PCT Filed: Apr. 28, 2016

(86) PCT No.: PCT/EP2016/059462
§ 371 (c)(1),
(2) Date: Oct. 26, 2017

(87) PCT Pub. No.: WO2016/174121
PCT Pub. Date: Nov. 3, 2016

(65) Prior Publication Data
US 2018/0118690 A1 May 3, 2018

(30) Foreign Application Priority Data
Apr. 29, 2015 (EP) .................... 15290112

(51) Int. Cl.
*C07D 231/16* (2006.01)
(52) U.S. Cl.
CPC .................. *C07D 231/16* (2013.01)
(58) Field of Classification Search
None
See application file for complete search history.

(56) References Cited

U.S. PATENT DOCUMENTS

| 5,675,016 A | 10/1997 | Gallenkamp et al. |
| 7,714,144 B2 * | 5/2010 | Neeff .................. B01J 31/0237 548/374.1 |
| 8,431,718 B2 | 4/2013 | Pazenok et al. |

FOREIGN PATENT DOCUMENTS

| WO | WO-2007/031212 | 3/2007 |
| WO | WO-2010/130797 | 11/2010 |
| WO | WO-2011/131615 | 10/2011 |

OTHER PUBLICATIONS

Finger, G.C. et al. (Dec. 5, 1956) "Aromatic Fluorine Compounds. VII. Replacement of Aromatic -CI and -NO$_2$ Groups by -F", *J. Am. Chem. Soc.*, 78(23):6034-6037.
International Search Report dated Jun. 13, 2016 for International Application No. PCT/EP2016/059462, filed Apr. 28, 2016, 5 pages.
Langlois et al. (1996) "Fluorination of Aromatic Compounds by Halogen Exchange with Fluoride Anions ("Halex" Reaction)", *Industrial Chemistry Library*, 8:244-292.
Written Opinion dated Jun. 13, 2016 for International Application No. PCT/EP2016/059462, filed Apr. 28, 2016, 4 pages.

* cited by examiner

*Primary Examiner* — Kamal A Saeed
(74) *Attorney, Agent, or Firm* — Morrison & Foerster LLP

(57) ABSTRACT

The present invention relates to a novel method for preparing 5-fluoro-1H-pyrazole-4-carbonyl fluorides by halogen exchange reaction of 5-chloro-1H-pyrazole-4-carbonyl chlorides with alkali metal fluorides, using non-polar solvents.

11 Claims, No Drawings

METHOD FOR PREPARING 5-FLUORO-1H-PYRAZOLE-4-CARBONYL FLUORIDES

CROSS REFERENCE TO RELATED APPLICATIONS

This application is the national stage of International Application No. PCT/EP2016/059462, filed internationally on Apr. 28, 2016, which claims the benefit of European Application No. 15290112.0, filed Apr. 29, 2015.

The present invention relates to a novel method for preparing 5-fluoro-1H-pyrazole-4-carbonyl fluorides by halogen exchange reaction of 5-chloro-1H-pyrazole-4-carbonyl chlorides with alkali metal fluorides.

5-Fluoro-1H-pyrazole-4-carbonyl fluorides are important intermediates in the synthesis of plant protection agents (see WO 2011/131615).

Patent applications U.S. Pat. No. 7,714,144 (equivalent to WO 2007/031212) and U.S. Pat. No. 5,675,016 disclose the exchange of chlorine for fluorine (halex process) starting from 5-chloro-1H-pyrazole-4-carbonyl chlorides in the presence of alkali metal fluorides. U.S. Pat. No. 5,675,016 discloses that solvents suitable to perform said reaction are all the polar aprotic organic solvents, and preferably sulphones such as sulpholanes. U.S. Pat. No. 7,714,144 discloses the preparation of 5-fluoro-1,3-dialkyl-1H-pyrazole-4-carbonyl fluorides from 5-chloro-1,3-dialkyl-1H-pyrazole-4-carbonyl chlorides in the presence of a polar aprotic solvent, more preferably sulpholane, dimethyl sulphoxide, dimethylacetamide or N-methylpyrrolidone. Both U.S. Pat. No. 7,714,144 and U.S. Pat. No. 5,675,016 disclose the use of aprotic polar solvents for halex reaction.

The use of aprotic polar solvents such as dimethyl formamide (DMF) or dimethyl sulfoxide (DMSO) for halex reaction is well known for the skilled man (Finger et al., J. Am. Chem. Soc., 1956, 78 (23), pp 6034-6037).

Nevertheless, use of aprotic polar solvents for halex reactions has also drawbacks for the economic viability of the methods, owing in particular to their partial water miscibility and the poor recyclability associated therewith. The workup of reactions in these solvents is usually possible only at high cost and/or it generates large amounts of waste water which has to be specially treated. As it is known that the water should be removed substantially from the reaction mixture for the success of the fluorination, it may be necessary or advantageous, in order to solve the issue of excess of water, to add to said aprotic polar solvent an additional low-boiling solvents which are able to form azeotropes with water, but said addition of further solvent to form a binary solvent is source of complexity and higher costs. Moreover, aprotic polar solvent are relatively expensive solvents.

The object of the present invention, therefore, is to find alternative solvents which do not have the disadvantages mentioned above for the preparation of 5-fluoro-1H-pyrazole-4-carbonyl fluorides by halogen exchange reaction from 5-chloro-1H-pyrazole-4-carbonyl chlorides with alkali metal fluorides.

It has now be shown very surprisingly by the present invention that non-polar solvents such as toluene, ethylbenzene, o-, m- and p-xylene (individually or as a mixture), mesitylene, chlorobenzene or dichlorobenzene can be used instead of aprotic polar solvent for preparing 5-fluoro-1H-pyrazole-4-carbonyl fluorides by halogen exchange reaction of 5-chloro-1H-pyrazole-4-carbonyl chlorides with alkali metal fluorides. Non-polar solvents are not only new and unexpected suitable solvents in said reaction, but in addition, they solve most of the disadvantages of aprotic polar solvents.

It is therefore a subject of the present invention to prepare 5-fluoro-1H-pyrazole-4-carbonyl fluorides of the formula (I)

wherein $R^1$ is $C_1$-$C_6$ alkyl, $R^2$ is $CH_3$, $CF_2H$, $CF_3$, $CF_2Cl$, $CCl_2F$, $C_2F_5$ or $C_3F_7$ by reacting 5-chloro-1H-pyrazole-4-carbonyl chlorides of the formula (II)

in which $R^1$ and $R^2$ are as above defined, with a fluorinating agent in the presence of a solvent selected among toluene, ethylbenzene, o-, m- and p-xylene (individually or as a mixture), mesitylene, chlorobenzene, and dichlorobenzene, in the presence of a phase transfer catalyst.

The fluorination of the corresponding 5-chloro-1H-pyrazole-4-carbonyl chlorides of formula (II) can take place in a stepwise manner (see Scheme 1), in which corresponding acid fluorides of formula (III) are initially formed and then the corresponding fluoroacid fluorides of formula (I) are formed. This means that at some point of the reaction all three compounds may be present at the same time. The relative accumulation of compounds of formula (I) in comparison to compounds of formula (III) is nevertheless increased by the presence of a phase transfer catalyst and a sufficient reaction time-period, and until total conversion into 5-fluoro-1H-pyrazole-4-carbonyl fluorides of formula (I) can be obtained. Alternatively, a mixture which is enriched in compounds of formula (I) can be obtained. Said compounds of formula (I) can then be isolated when needed. Isolation could be done for example by distillation of solvent (e.g. Chlorobenzene) and then distillation of desired compound at higher temperatures, under conditions which can be determined by the skilled man (when R1=CH3 and R2=CHF2 the following distillation conditions could applied: jacket: 177° C.-197° C./sump: 165° C./b.p.: 130° C.//pressure=18 mbar).

The reaction could also be conducted in two stages. In this case, compound (III), which can also be isolated, is initially formed under milder conditions, usually without addition of phase transfer catalysts. This can be carried out with HF or trialkylamine-n-hydrofluorides (n=1-5). In a second step, this compound (III) is used as reactant for the preparation of (I), in the presence of a phase transfer catalyst.

Scheme 1

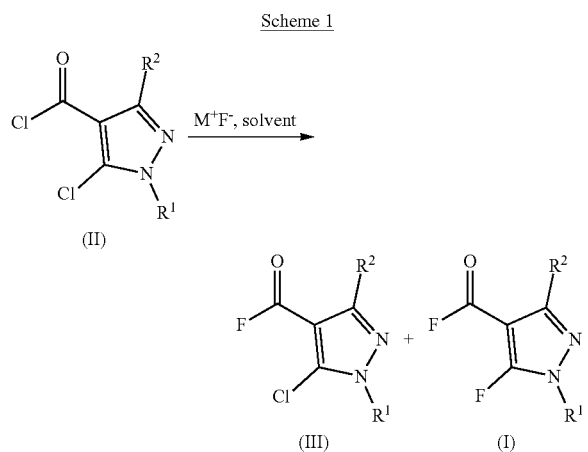

The methods of the invention, compared to the prior art, are more economical, more environmentally friendly and technically distinctly easier to implement. Recovery of aprotic solvents of prior art, such as sulpholane, would be considerably more difficult, mostly due to the very high boiling point (e.g. sulpholane: b.p. 285° C.) and/or partial decomposition of solvents such as dimethylacetamide and dimethylformamide. A further disadvantage in using aprotic solvents such as sulpholane is that some pyrazoles are in the same boiling range as them and therefore separation by distillation is difficult. By using the solvents used in the present invention, separation by distillation is possible without any problem.

Moreover, this reaction procedure enables substantially lower temperatures which allows a simplified and more cost-effective plant design. Owing to a reaction proceeding largely selectively under these conditions, the yields are in very good ranges (80-90%) for halex reactions and exceed those reactions conducted in aprotic polar solvents.

The formula (II) provides a general definition of the compounds used as starting materials for carrying out the method according to the invention. The residue $R^1$ is preferably methyl, ethyl, n-propyl, isopropyl, butyl or pentyl, preferably methyl or ethyl and more preferably methyl. The residue $R^2$ is methyl or, $CF_2H$, $CF_3$, $CF_2Cl$, $CCl_2F$, $C_2F_5$, $C_3F_7$. Particular preference for $R^2$ is given to methyl and $CF_2H$.

5-chloro-1H-pyrazole-4-carbonyl chlorides of formula (II) can be prepared, for example, by oxidative chlorination starting from the corresponding aldehyde. The prior art is described in WO 2008/086962 and WO 2011/061205.

A further advantage of the procedure according to the invention is that the resulting solutions in organo-chlorine solvents customary in chlorinations, such as chlorobenzene, dichlorobenzene etc., may be used directly without complex solvent exchange or even isolation of the acid chloride in the halex step.

The fluorination of the compounds of the formula (II) takes place according to the invention in the presence of a fluorinating agent of the formula (IV), $$M^+F^- \qquad (IV)$$

In formula (IV), W is an alkali metal cation or ammonium cation, preferably $Li^+$, $Na^+$, $K^+$, $Cs^+$, $alkyl_4N^+$, or a mixture of the same, where alkyl is $C_1$-$C_4$-alkyl. Particular preference is given to using an alkali metal fluoride as fluorinating agent, in particular potassium fluoride.

Potassium fluoride is a known chemical in synthesis and is commercially available.

Quarternary ammonium, phosphonium compounds or amidophosphonium salts are suitable as phase transfer catalysts for carrying out the method according to the invention. Examples include compounds such as tetramethylammonium chloride or bromide, tetrabutylammonium chloride, trimethylbenzylammonium chloride, tetrabutylammonium bromide, tricaprylmethylammonium chloride (Aliquat 336), methyltrioctylammonium chloride, tributylmethylammonium chloride (Aliquat 175), tetrabutylphosphonium chloride, tetrabutylphosphonium bromide, tetraphenylphosphonium chloride, ionic liquids, including in particular trihexyltetradecylphosphonium chloride, bromide, dicyanamide, hexafluorophosphate or tetrafluoroborate, tetrakis(dimethylamino)phosphonium chloride or bromide, tetrakis(diethylamino)phosphonium chloride or bromide, tris(diethylamino)(dimethylamino)phosphonium chloride or bromide, tris(dimethylamino)(dihexylamino)phosphonium chloride or bromide, tris(diethylamino)(dihexylamino)phosphonium chloride or bromide, hexaalkylguanidinium salts (Alkyl=$C_1$-$C_8$) or polyethylene glycol dimethyl ethers having chain lengths r of 6 to 17 and a mean molar mass of 500 g/mol, urotroponium salts, octaalkyloxamidinium chloride and bromide (alkyl=$C_1$-$C_4$). Preference is given to tributylmethylammonium chloride (Aliquat 175), methyltrioctylammonium chloride, tricaprylmethylammonium chloride (Aliquat 336), hexabutyl guanidinium chloride, hexaethyl guanidinium chloride, hexamethyl guanidinium chloride, tetraphenylphosphonium bromide and tetrabutylphosphonium chloride. Particular preference is given to hexamethyl guanidinium chloride, hexaethyl guanidinium chloride and tetrabutylphosphonium chloride.

The use of non-polar solvents selected among toluene, ethylbenzene, o-, m- and p-xylene (individually or as a mixture), mesitylene, chlorobenzene and dichlorobenzene is suitable for carrying out the method according to the invention. Preference is given to aromatic solvents selected among s toluene, o-, m- and p-xylene (individually or as a mixture), mesitylene, chlorobenzene and dichlorobenzene and particular preference is given to toluene, o-, m- and p-xylene (individually or as a mixture) and chlorobenzene.

The method according to the invention (scheme 1) is preferably carried out within a temperature range of 20° C. to 200° C., more preferably at temperatures of 80° C. to 180° C., particularly preferably at temperatures of 100° C. to 160° C.

The reaction time is not critical and may, according to the batch size and temperature, be selected within a range between one and several hours, preferably between 2 and 20 hours, between 3 and 16 hours, between 4 and 16 hours.

To carry out the method according to the invention, 2.0-5.0 mol, preferably 2.2 mol to 4.0 mol, particularly preferably 2.5 to 3.5 mol of alkali metal fluoride is used per 1 mole of the compounds of the formula (II).

To carry out the method according to the invention, 0.005-0.5 mol, preferably 0.01 mol to 0.25 mol, particularly preferably 0.02 to 0.1 mol of phase transfer catalyst is used per 1 mole of the compounds of the type (II).

For the workup, the resulting reaction mixture is freed from the alkali metal salts by filtration. The product is then freed from the solvent by means of distillation and can be purified by a further distillation. Naturally, it is possible without further workup to proceed with the solutions obtained to the next chemical step.

PREPARATION EXAMPLES

Example 1

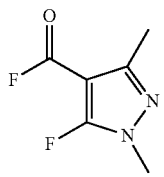

5-Chloro-1-methyl-3-methyl-1H-pyrazole-4-carbonyl chloride (10 g, 0.05 mol), KF (8.8 g, 0.15 mol) and hexamethyl guanidinium chloride (0.454 g, 2.53 mmol) in chlorobenzene (50 g) were stirred under argon at 140° C. for 15.5 hours. The inorganic salts were then filtered off and the chlorobenzene distilled off under reduced pressure. 25.8 g of 5-fluoro-1,3-dimethyl-1H-pyrazole-4-carbonyl fluoride were obtained. (Content: 64.4%, Yield: 65.3% of theory).
GC/MS: m/z=160.

Example 2

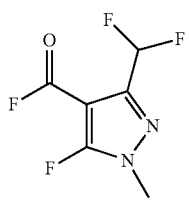

5-Chloro-1-methyl-3-difluoromethyl-1H-pyrazole-4-carbonyl chloride (40 g, 85.5 mmol, 49% in chlorobenzene), potassium fluoride (15.9 g, 273.8 mmol) and hexabutyl guanidinium chloride (1.85 g, 4.28 mmol) were stirred under argon at 135° C. for 8.5 hours. The resulting suspension was freed from salts by filtration. 77 g of a solution in chlorobenzene of 5-fluoro-1-methyl-3-difluoromethyl-1H-pyrazole-4-carbonyl fluoride were obtained (Content: 19.9%, Yield: 91.5% of theory).
GC/MS: m/z=196.
$^1$H-NMR (CDCl3): δ=3.86 (s), 6.77 (t).

Example 3

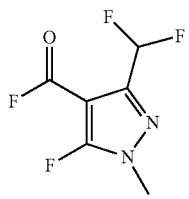

5-Chloro-1-methyl-3-difluoromethyl-1H-pyrazole-4-carbonyl chloride (311 g, 45% solution in chlorobenzene, 0.61 mol), KF (113.3 g, 1.94 mmol) and hexamethyl guanidinium chloride (5.47 g, 0.03 mol) were stirred under argon at 138° C. for 6 hours. The inorganic salts were then filtered off and the filter cake washed with 250 g of chlorobenzene. 704 g of a solution in chlorobenzene of 5-fluoro-1-methyl-3-difluoromethyl-1H-pyrazole-4-carbonyl fluoride were obtained (Content: 16.1%, Yield: 95.1% of theory).

Example 4

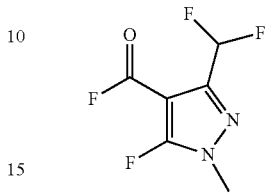

5-Chloro-1-methyl-3-difluoromethyl-1H-pyrazole-4-carbonyl chloride (5.24 g, 22.8 mmol), KF (4.25 g, 73 mmol) and hexamethyl guanidinium chloride (0.2 g, 1.11 mmol) in toluene (20 g) were stirred under argon at 120° C. for 10 hours. A sample was analysed. GC: 75% conversion to 5-fluoro-1-methyl-3-difluoromethyl-1H-pyrazole-4-carbonyl fluoride.

Example 5

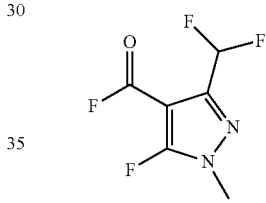

5-Chloro-1-methyl-3-difluoromethyl-1H-pyrazole-4-carbonyl chloride (2.28 g, 9.93 mmol), KF (1.85 g, 31.7 mmol) and hexamethyl guanidinium chloride (89 mg, 0.50 mmol) in xylene (10 g) were stirred under argon at 135° C. for 4 hours. A sample was analysed. GC: 100% conversion to 5-fluoro-1-methyl-3-difluoromethyl-1H-pyrazole-4-carbonyl fluoride.

Example 6

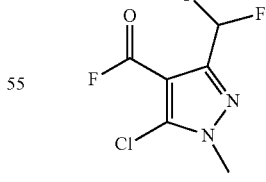

5-Chloro-1-methyl-3-difluoromethyl-1H-pyrazole-4-carbonyl chloride (29.3 g, 127 mmol), potassium hydrogen difluoride (16 g, 204 mmol) in o-dichlorobenzene (63 g) were stirred under argon at 120° C. for 2 hours. A sample was analysed. GC: >99% conversion to 5-chloro-1-methyl-3-difluoromethyl-1H-pyrazole-4-carbonyl fluoride.
GC-MS: [M$^+$]=212.

Example 7

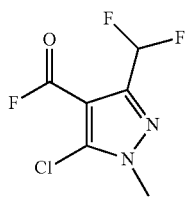

5-Chloro-1-methyl-3-difluoromethyl-1H-pyrazole-4-carbonyl chloride (1.36 g, 5.96 mmol), potassium fluoride (1.1 g, 19 mmol) in chlorobenzene (10 g) were stirred under argon at 130° C. for 2 hours. A sample was analysed. GC:>99% conversion to 5-chloro-1-methyl-3-difluoromethyl-1H-pyrazole-4-carbonyl fluoride.

Example 8

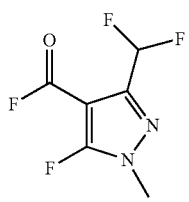

5-Chloro-1-methyl-3-difluoromethyl-1H-pyrazole-4-carbonyl chloride (100 g, 0.21 mmol, 49% in chlorobenzene), potassium fluoride (39.8 g, 0.68 mol) and tetrabutylphosphonium chloride (3.15 g, 11 mmol) were stirred under argon at 135° C. for 6 hours. The resulting suspension was freed from salts by filtration and washed with chlorobenzene. 217.9 g of a solution in chlorobenzene of 5-fluoro-1-methyl-3-difluoromethyl-1H-pyrazole-4-carbonyl fluoride were obtained (Content: 17.8%, Yield: 92.3% of theory).

Example 9

Further experiments with various phase transfer catalysts were carried out. The conversions were checked by GC and are summarized in Tables 1-4 below:

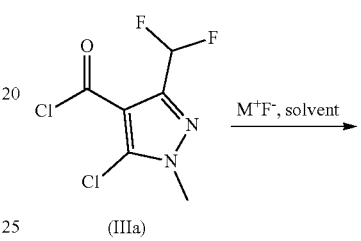

(IIIa)

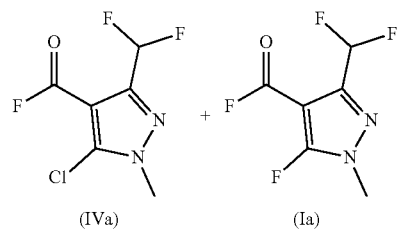

(IVa)　　(Ia)

TABLE 1

Screening of various phase transfer catalysts (IIIa was charged with 3 eq. of KF and 5 mol % phase transfer catalyst in chlorobenzene and stirred at 135-140° C. for 5 h, conversion check by GC)

| Time [h] | IVa | Ia | IVa | Ia | IVa | Ia | IVa | Ia | IVa | Ia |
|---|---|---|---|---|---|---|---|---|---|---|
| | 1 | | 2 | | 3 | | 4 | | 5 | |
| Tetrabutylphosphonium bromide | 88.1 | 11.9 | 64.1 | 35.9 | 52 | 48 | 44.6 | 55.4 | 40.8 | 59.2 |
| Tetrabutylphosphonium chloride | 73.4 | 26.6 | 36.6 | 63.4 | 16.9 | 83.1 | 3.2 | 96.8 | 0 | 100 |
| Aliquat 336 | 52 | 48 | 24.6 | 75.4 | 11.4 | 88.6 | 5.9 | 94.1 | 4.2 | 95.8 |
| Tetrabutylammonium hydrogen sulphate | 95.2 | 4.8 | 84.2 | 15.8 | 70.3 | 29.7 | 60.3 | 39.7 | 54.6 | 45.4 |
| Tetramethylammonium chloride | 90.2 | 9.8 | 75.2 | 24.8 | 62.7 | 37.3 | 52.6 | 47.4 | 45.2 | 54.8 |
| Tetraphenylphosphonium bromide | 45.8 | 54.2 | 27.5 | 72.5 | 13.8 | 86.2 | 5 | 95 | 0 | 100 |
| Tetrabutylammonium bromide | 61.5 | 38.5 | 41 | 59 | 28.1 | 71.9 | 20.6 | 79.4 | 17.7 | 82.3 |
| Benzyltriethylammonium chloride | 71.5 | 28.5 | 61.3 | 38.7 | 55.6 | 44.4 | 52.3 | 47.7 | 49.7 | 50.3 |
| 1-Butyl-3-methylimidazolium chloride | 85.1 | 14.9 | 83.5 | 16.5 | 81.3 | 18.7 | 79.4 | 20.6 | 78 | 22 |
| No addition | 100 | 0 | 100 | 0 | 100 | 0 | 100 | 0 | 100 | 0 |

TABLE 2

Screening of various trihexyltetradecylphosphonium salts (conversion check by GC), 1 g IIIa, 3 eq. of KF, 135-140° C., 5 mol % phase transfer catalyst in xylene

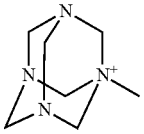

| | 1h | | 2h | | 3h | | 4h | | 5h | |
|---|---|---|---|---|---|---|---|---|---|---|
| X = | IVa | Ia | IVa | Ia | IVa | Ia | IVa | Ia | IVa | Ia |
| Br | 46.4 | 53.6 | 15.3 | 84.7 | 7.8 | 92.2 | 5.7 | 94.3 | 4.3 | 95.7 |
| Cl | 53.5 | 46.5 | 12.1 | 77.9 | 9.9 | 90.1 | 5.3 | 94.7 | 3.9 | 96.1 |
| decanoates | 93.8 | 6.2 | 67.7 | 32.3 | 55.9 | 44.1 | 47.7 | 52.3 | 44.4 | 55.6 |
| dicyanamide | 78.5 | 21.5 | 51.6 | 48.4 | 37.1 | 62.9 | 26 | 74 | 20.5 | 79.5 |
| $PF_6$ | 100 | 0 | 100 | 0 | 98.9 | 1.1 | 98.2 | 1.8 | 97.6 | 2.4 |
| $BF_4$ | 84.1 | 15.9 | 65.9 | 34.1 | 51.8 | 48.2 | 37 | 63 | 27.5 | 72.5 |
| Hexamethyl guanidinium chloride | 57.5 | 42.5 | 22.5 | 77.5 | 6.1 | 93.9 | 0 | 100 | 0 | 100 |

TABLE 3

Screening of various trihexyltetradecylphosphonium salts (conversion check by GC), 1 g IIIa, 3 eq. of KF, 135-140° C., 5 mol % phase transfer catalyst in chlorobenzene

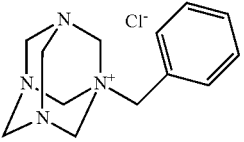 [SMILES: c1ccc(C[N+]23CN4CN(CN(C4)C2)C3)cc1 ; [Cl-]]

| | 1h | | 2h | | 3h | | 4h | | 5h | |
|---|---|---|---|---|---|---|---|---|---|---|
| X = | IVa | Ia | IVa | Ia | IVa | Ia | IVa | Ia | IVa | Ia |
| Br | 53.4 | 46.6 | 22.3 | 77.7 | 6.5 | 93.5 | 1.3 | 98.7 | 0.8 | 99.2 |
| Cl | 61.9 | 38.1 | 27.7 | 72.3 | 8.9 | 91.1 | 1.5 | 98.5 | 1 | 99 |
| decanoates | 92.1 | 7.9 | 43.7 | 56.3 | 22.9 | 77.1 | 12.2 | 87.8 | 7.8 | 92.2 |
| dicyanamide | 74.2 | 25.8 | 37.7 | 62.3 | 18.5 | 81.5 | 7.9 | 92.1 | 3.2 | 96.8 |
| $PF_6$ | 100 | 0 | 100 | 0 | 98.9 | 1.1 | 98.3 | 1.7 | 97.7 | 2.3 |
| $BF_4$ | 94.4 | 5.6 | 75.8 | 24.2 | 63.7 | 36.3 | 52.5 | 47.5 | 43.1 | 56.9 |
| Hexamethyl guanidinium chloride | 55.2 | 44.8 | 27.5 | 72.5 | 10.4 | 89.6 | 2.2 | 97.8 | 0 | 100 |

TABLE 4

Urotropin-based phase transfer catalysts and octamethyloxamidinium dibromide, 1 g IIIa, 5 mol % phase transfer catalyst in chlorobenzene

| Phase transfer catalyst | Conversion to Ia |
|---|---|
| 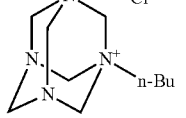 | 51.1 |
| | 4.4 |
| 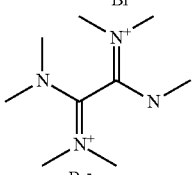 | 12.2 |
| | 100 |

The invention claimed is:

1. A process for preparing a 5-fluoro-1H-pyrazole-4-carbonyl fluoride of formula (I)

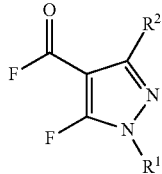

(I)

wherein:
$R^1$ is $C_1$-$C_6$-alkyl; and
$R^2$ is $CF_2H$, $CF_3$, $CF_2Cl$, $CCl_2F$, $C_2F_5$ or $C_3F_7$;
comprising reacting a 5-chloro-1H-pyrazole-4-carbonyl chloride of formula (II)

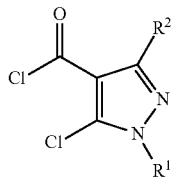

(II)

wherein $R^1$ and $R^2$ are as defined for formula (I);
with a fluorinating agent in the presence of a solvent selected from the group consisting of toluene, ethylbenzene, o-, m- and p-xylene (individually or as a mixture), mesitylene, chlorobenzene, and dichlorobenzene, in the presence of a phase transfer catalyst, to form the 5-fluoro-1H-pyrazole-4-carbonyl fluoride of formula (I).

2. The process according to claim 1, wherein $R^1$ is methyl, ethyl, n-propyl, isopropyl, butyl or pentyl.

3. The process according to claim 2, wherein $R^1$ is methyl or ethyl.

4. The process according to claim 3, wherein $R^1$ is methyl.

5. The process according to claim 1, wherein $R^2$ is $CF_2H$.

6. The process according to claim 1, wherein the fluorinating agent is of formula (IV), $$M^+F^-$$ (IV), wherein $M^+$ is an alkali metal cation or ammonium cation.

7. The process according to claim 6, wherein the fluorinating agent is potassium fluoride.

8. The process according to claim 1, wherein the phase transfer catalyst is selected from the group consisting of tributylmethylammonium chloride (Aliquat 175), methyltrioctylammonium chloride, tricaprylmethylammonium chloride (Aliquat 336), hexabutylguanidinium chloride, hexaethyl guanidinium chloride, hexamethyl guanidinium chloride, tetraphenylphosphonium bromide and tetrabutylphosphonium chloride.

9. The process according to claim 8, wherein the phase transfer catalyst is hexamethyl guanidinium chloride, hexaethyl guanidinium chloride or tetrabutylphosphonium chloride.

10. The process according to claim 1, wherein the solvent is selected from the group consisting of toluene, o-, m- and p-xylene (individually or as a mixture), mesitylene, chlorobenzene and dichlorobenzene.

11. The process according to claim 9, wherein the solvent is selected from the group consisting of toluene, o-, m- and p-xylene (individually or as a mixture) and chlorobenzene.

* * * * *